United States Patent [19]

Haas et al.

[11] 4,400,331
[45] Aug. 23, 1983

[54] DIALKOXY-PHOSPHONYL-N-ALKYL-FORMIC ACID AMIDES

[75] Inventors: Peter Haas, Haan; Heinz Müller, Leverkusen; Peter Seifert, Bergisch Gladbach; Kuno Wagner, Leverkusen; Kurt Findeisen, Odenthal; Klaus König, Leverkusen, all of Fed. Rep. of Germany

[73] Assignee: Bayer Aktiengesellschaft, Leverkusen, Fed. Rep. of Germany

[21] Appl. No.: 342,544

[22] Filed: Jan. 25, 1982

Related U.S. Application Data

[62] Division of Ser. No. 185,870, Sep. 11, 1980, Pat. No. 4,328,321.

[30] Foreign Application Priority Data

Sep. 17, 1979 [DE] Fed. Rep. of Germany ....... 2937509

[51] Int. Cl.³ ................................. C07F 9/40
[52] U.S. Cl. ..................................... 260/932; 260/943
[58] Field of Search ............................... 260/943, 932

[56] References Cited

FOREIGN PATENT DOCUMENTS 25572 3/1981 European Pat. Off. ............ 260/932

OTHER PUBLICATIONS

Kuznetsov et al., "Chemical Abstracts", vol. 56, (1962), 14037i.

*Primary Examiner*—Anton H. Sutto
*Attorney, Agent, or Firm*—Gene Harsh; Joseph C. Gil; Richard A. Elder

[57] ABSTRACT

The present invention relates to a process for the preparation of polyurethane foams capable of being flame laminated and high frequency welded, comprising reacting:
(a) polyisocyanate,
(b) a compound having a molecular weight of from 400 to 10,000 containing at least two isocyanate-reactive hydrogen atoms and
(c) a dialkoxy-phosphonyl-N-alkyl-formic acid amide of the formula:

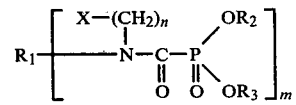

wherein
m represents an integer of from 1 to 3,
n represents an integer of from 0 to 8,
X represents halogen, hydrogen, $C_1$ to $C_6$ alkyl, -OR, or

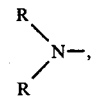

R represents $C_1$ to $C_6$ alkyl,
$R_1$ represents hydrogen, $C_1$ to $C_{10}$ alkyl, $C_1$ to $C_{10}$ alkylene, $C_6$ to $C_{10}$ aryl or $C_6$ to $C_{10}$ arylene, and
$R_2$ and $R_3$, which may be the same or different, represent $C_1$ to $C_{10}$ alkyl in the presence of water and/or blowing agent.

The present invention also relates to dialkoxy-phosphonyl-N-formic acid amides.

1 Claim, No Drawings

DIALKOXY-PHOSPHONYL-N-ALKYL-FORMIC ACID AMIDES

This application is a division, of application Ser. No. 185,870, filed Sept. 11, 1980, now U.S. Pat. No. 4,328,321.

BACKGROUND OF THE INVENTION

Foams containing urethane groups which are obtained by the reaction of polyisocyanates with polyether polyols and/or polyester polyols are known and widely used. The possibilities of using polyurethane foams are, however, severely restricted in certain fields due to their complete or relative inability to be high frequency welded or flame laminated. Areas in which these properties are particularly important include, for example, the manufacture of door facings in cars which requires the welding of a sheet of foam to another or to other materials, the production of quilted effects and the manufacture of shaped articles. Flame laminating is also used to produce composite systems containing textiles, e.g. as upholstery material which is subsequently shaped or molded by high frequency welding.

It is known that foams containing groups which are capable of being high frequency welded can be produced by reacting compounds which have several active hydrogen atoms with polyisocyanates in the presence of water and/or blowing agents, emulsifiers, stabilizers, catalysts and other auxiliary agents and compounds which render them capable of high frequency welding and flame laminating, or to subject the finished foams to an after-treatment which renders them capable of high frequency welding.

Compounds which confer such a high frequency welding quality include, for example, powdered polyvinyl acetates, polyvinyl chlorides and copolymers (Belgian Pat. No. 719,875), thermoplastic polymers such as ethylene vinyl acetate, cellulose derivatives such as ethyl or benzyl cellulose, acrylate polymers and polyethylene (German Offenlegungsschrift No. 1,769,583).

The ability of polyurethane foams to be high frequency welded can also be increased by the addition of water-soluble inorganic or organic salts such as sodium thiosulfate or sodium acetate (German Offenlegungsschrift 1,669,888). An improvement in the high frequency welding characteristics of polyurethane foams by after-treatment has been described, for example, in French Pat. Nos. 1,329,849; 1,344,444 and 1,343,681.

The addition of powders of thermoplast solutions to the starting materials used for the production of polyurethanes has certain disadvantages. To produce a significant effect, it is necessary to use substantial quantities, but this entails technical difficulties, for example due to the resulting sharp increase in viscosity, and leads to production difficulties. Moreover, the properties of the foams are adversely affected by these products. Subsequent impregnation of the finished foams is also not without its problems. It is very difficult, for example, to impregnate very thick layers of foam. Moreover, removal of the solvent and drying of the after-treated foam generally entails some technical difficulties and, in any case, after-treatment requires an additional operating step.

The known methods for the production of polyurethane foams which can be high frequency welded entail considerable technical (and financial) cost and result in foams which have unsatisfactory properties. Furthermore, polyether foams which have been treated by these methods are not left in a state in which they can be flame laminated, but require the addition of compounds such as derivatives of phosphorous or phosphoric acid at the stage of foaming. These compounds generally have a deleterious effect on the mechanical properties of the product.

It has now surprisingly been found that the additives according to the present invention substantially improve the capacity of polyurethane foams to be high frequency welded without having any adverse effect on their properties such as compression resistance and pressure deformation residue.

DESCRIPTION OF THE INVENTION

The present invention relates to a process for the preparation of polyurethane foams capable of being flame laminated and high frequency welded, comprising reacting
 (a) polyisocyanate,
 (b) a compound having a molecular weight of from 400 to 10,000 containing at least two isocyanate-reactive hydrogen atoms, and
 (c) a dialkoxy-phosphonyl-N-alkyl-formic acid amide of the formula:

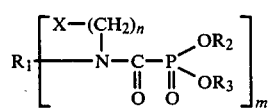

wherein
 m represents an integer of from 1 to 3,
 n represents an integer of from 0 to 8,
 X represents halogen, hydrogen, $C_1$ to $C_6$ alkyl, -OR, or

R represents $C_1$ to $C_6$ alkyl,
 $R_1$ represents hydrogen, $C_1$ to $C_{10}$ alkyl, $C_1$ to $C_{10}$ alkylene, $C_6$ to $C_{10}$ aryl or $C_6$ to $C_{10}$ arylene, and
 $R_2$ and $R_3$, which may be the same or different, represent $C_1$ to $C_{10}$ alkyl in the presence of water and/or blowing agent.

Chain lengthening agents having a molecular weight of from 32 to 400 may also be used in the reaction. Catalysts, foam stabilizers and other additives and auxiliary agents may also be present.

The preferred dialkoxy-phosphonyl-N-alkyl-formic acid amides are

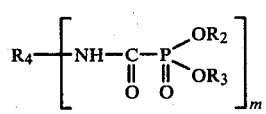

wherein
 $R_4$ represents $C_1$ to $C_{10}$ alkyl, $C_1$ to $C_{10}$ alkylene, $C_6$ to $C_{10}$ aryl or $C_6$ to $C_{10}$ arylene and
 $R_2$, $R_3$ and m are defined as above.

The present invention also relates to novel dialkoxy-phosphonyl-N-alkyl-formic acid amides corresponding to the following formulae:

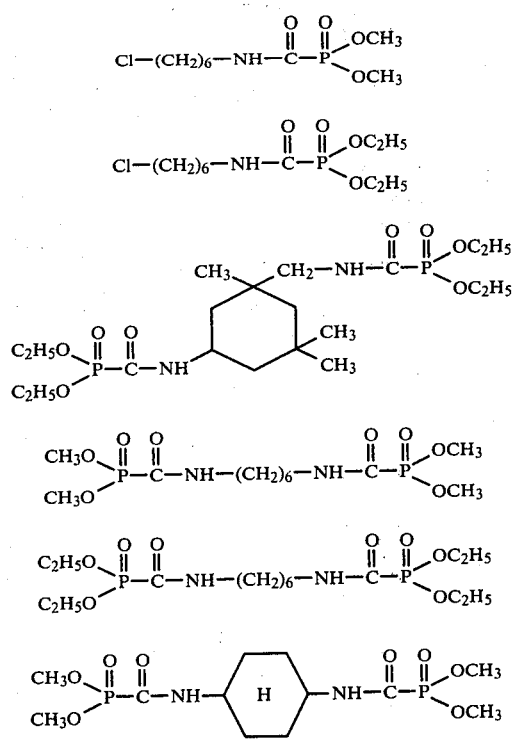

The compounds used according to the present invention which render polyurethane foams capable of being flame laminated and high frequency welded may be prepared by known methods, e.g. by the reaction of carbamic acid chlorides with trialkylphosphites (T. Reetz, Am. Soc. 77, 3513 [1955]; Arbusov, Izv. Akad. SSSR, 1952, 847 [C.A. 47, 10457, 1953] or, for example, by the addition of isocyanates to dialkylphosphites in accordance with the following reaction scheme:

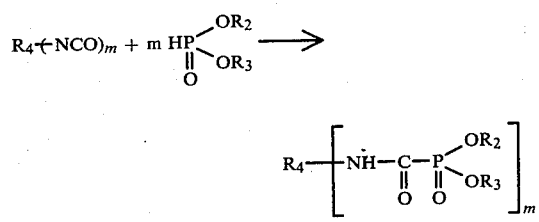

wherein
$R_4$, $R_2$, $R_3$ and m are defined as above. Compounds corresponding to general formula II are preferred.

The isocyanates used may be aliphatic, cycloaliphatic or aromatic monoisocyanates such as methyl, methoxymethyl, ethyl, n-butyl, n-hexyl, cyclohexyl, phenyl or naphthyl isocyanate as well as aliphatic, cycloaliphatic or aromatic diisocyanates and triisocyanates such as those mentioned, for example, in German Offenlegungsschrift No. 2,737,951, pages 24–26.

The following are mentioned as examples of dialkoxy-phosphonyl-N-alkyl-formic acid amides which may be used according to the present invention:

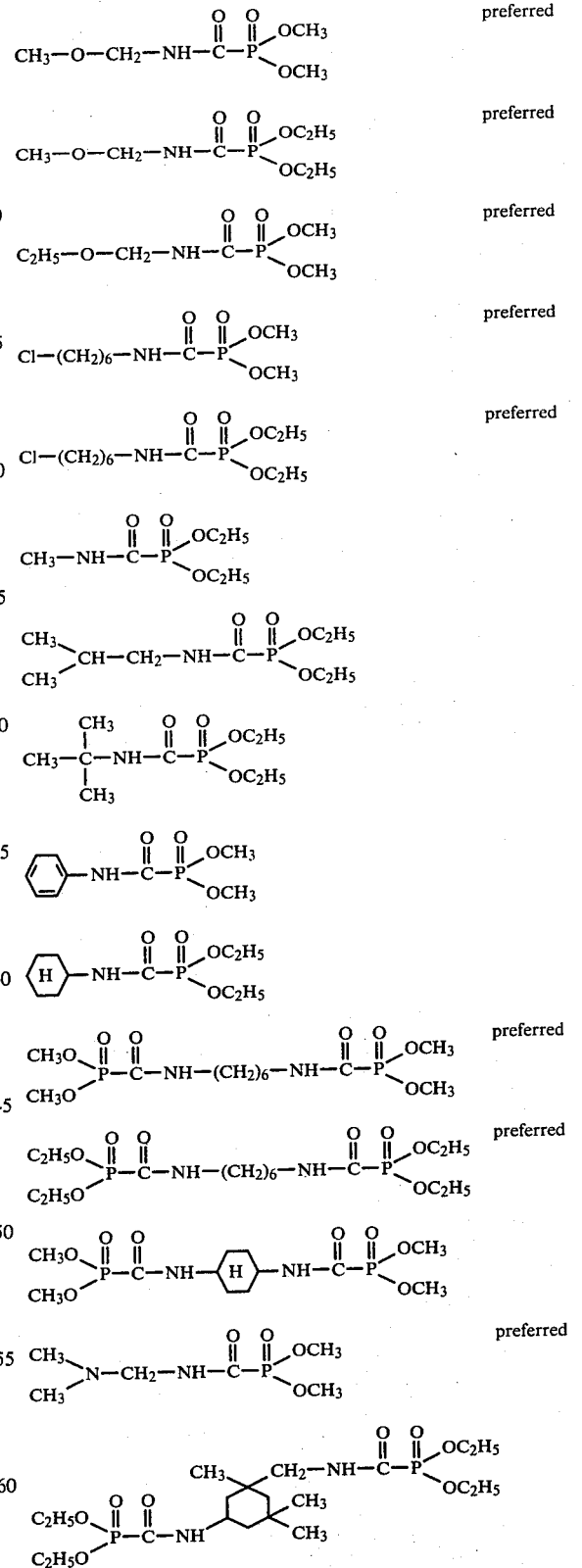

The quantity of bis-alkoxy-phosphonyl-alkylformic acid amides used according to the present invention is generally from 0.1 to 10.0 parts by weight, preferably from 0.5 to 5.0 parts by weight, based on 100 parts by weight of the compound having a molecular weight of from 400 to 10,000 which has at least two active hydrogen atoms.

When added to polyurethane foams, these compounds corresponding to the above general formulae I and II render the foams capable of being flame laminated as well as enabling them to be readily welded by high frequency welding to textile surface layers made, for example, of polyamide, polyacrylonitrile or polyurethane fabrics as well as to covering foils, e.g. of PVC.

For a given welding energy and pressure, the welding time required for producing a smooth, opaque welding seam is considerably reduced (see the Examples). The welding experiments were carried out on polyamide foam sandwich systems having a total thickness of 10 mm or on two sheets of foam each having a thickness of 10 mm.

1. The following polyisocyanates may be used in the preparation of the polyurethane foams: aliphatic, cycloaliphatic, araliphatic, aromatic and heterocyclic polyisocyanates as described, for example, by W. Siefken in Justus Liebigs Annalen der Chemie, 562, pages 75 to 136, for example those corresponding to the following general formula

wherein n=2-4, preferably 2, and

Q represents an aliphatic hydrocarbon group having 2-18, preferably 6-10 carbon atoms, a cycloaliphatic hydrocarbon group having 4-15, preferably 5-10 carbon atoms, an aromatic hydrocarbon group having 6-15, preferably 6-13 carbon atoms, or an araliphatic hydrocarbon group having 8-15, preferably 8-13 carbon atoms, e.g. those described in German Offenlegungsschrift No. 2,737,951, pages 24-26.

The preferred polyisocyanates are aromatic polyisocyanates.

It is, in most cases, particularly preferred to use commercially readily available polyisocyanates such as 2,4- and 2,6-tolylene diisocyanate and any mixtures of these isomers ("TDI"), polyphenylpolymethylene polyisocyanates which may be prepared by aniline/formaldehyde condensation followed by phosgenation ("crude MDI") and polyisocyanates containing carbodiimide groups, urethane groups, allophanate groups, isocyanurate groups, urea groups or biuret groups ("modified polyisocyanates"), particularly those modified polyisocyanates which are derived from 2,4- and/or 2,6-tolylene diisocyanates or from 4,4'- and/or 2,4'-diphenylmethane diisocyanates.

2. The starting components also include compounds containing at least two isocyanate-reactive hydrogen atoms, generally having a molecular weight of from 400 to 10,000. These include compounds containing amino groups, thiol groups or carboxyl groups but are preferably hydroxyl compounds especially compounds having 2-8 hydroxyl groups and particularly those having a molecular weight within the range of from 1,000 to 6,000, preferably from 2,000 to 4,000. Examples include hydroxyl polyesters, hydroxyl polyethers, hydroxyl polythioethers, hydroxyl polyacetals, hydroxyl polycarbonates and hydroxyl polyester amides having at least 2, generally 2-8, preferably 2-4, hydroxyl groups such as the hydroxyl compounds known for the production of both homogeneous and cellular polyurethanes.

Suitable compounds have been described, for example, in German Offenlegungsschrift No. 2,737,951, pages 26-29.

The polyhydroxyl compounds may be modified in numerous ways before they are used in the polyisocyanate polyaddition process. According to German Offenlegungsschriften Nos. 2,210,839 (U.S. Pat. No. 3,849,515) and 2,544,195, a mixture of various polyhydroxyl compounds (e.g. of a polyether polyol and a polyester polyol) may be condensed by etherification in the presence of a strong acid to produce a relatively high molecular weight polyol built up of various segments linked together by ether bridges. Alternatively, amide groups may be incorporated in the polyhydroxyl compounds according to German Offenlegungsschrift No. 2,559,372 or triazine groups may be introduced by a reaction with polyfunctional cyanic acid esters according to German Offenlegungsschrift No. 2,620,487. Polyhydroxyl compounds containing guanidine, phosphonoformamidine or acyl urea groups are obtained by the reaction of a polyol with a less than equivalent quantity of a diisocyanatocarbodiimide followed by reaction of the carbodiimide group with an amine, amide, phosphite or carboxylic acid (German Offenlegungsschriften Nos. 2,714,289; 2,714,292 and 2,714,293). It is sometimes of particular interest to convert the relatively high molecular weight polyhydroxyl compounds either partly or completely into the corresponding anthranilic acid esters by a reaction with isatoic acid anhydride as described in German Offenlegungsschriften Nos. 2,019,432 and 2,619,840 or in U.S. Pat. Nos. 3,808,250; 3,975,428 and 4,016,143. Relatively high molecular weight compounds having aromatic amino end groups are obtained by this reaction.

According to German Offenlegungsschrift No. 2,546,536 and U.S. Pat. No. 3,865,791, relatively high molecular weight compounds containing amino end groups are obtained by the reaction of isocyanate prepolymers with hydroxyl-containing enamines, aldimines or ketimines, followed by hydrolysis. Other methods of preparing relatively high molecular weight compounds having amino end groups or hydrazide end groups have been described in German Offenlegungsschrift No. 1,694,152 (U.S. Pat. No. 3,625,871).

Polyhydroxyl compounds containing high molecular weight polyadducts or polycondensates or polymers in a finely dispersed or dissolved form may also be used according to the present invention (see e.g. German Offenlegungsschrift No. 2,737,951, page 31).

Polyhydroxyl compounds which have been modified with vinyl polymers are also suitable for the process according to the present invention. These may be obtained, for example, by the polymerization of styrene and acrylonitrile in the presence of polyethers (U.S. Pat. Nos. 3,383,351; 3,304,273; 3,523,093 and 3,110,695 and German Auslegeschrift No. 1,152,536) or of polycarbonate polyols (German Pat. No. 1,769,795 or U.S. Pat. No. 3,637,909). Synthetic materials having exceptionally high flame resistance are obtained when using polyether polyols which have been modified according to German Offenlegungsschriften Nos. 2,442,101; 2,644,922 and 2,646,141 by graft polymerization with vinyl phosphonic acid esters and optionally (meth)acrylonitrile, (meth)acrylamide or OH functional (meth)acrylic acid esters. Polyhydroxyl compounds into which carboxyl groups have been introduced by radical graft polymerization with unsaturated carboxylic acid and optionally other olefinically unsaturated monomers (German Offenlegungsschriften Nos. 2,714,291; 2,739,620 and 2,654,746) are particularly advantageously used in combination with mineral fillers.

Representatives of the above-mentioned compounds to be used according to the present invention have been described, for example, in High Polymers, Volume XVI, "Polyurethanes: Chemistry and Technology" by Saunders-Frisch, Interscience Publishers, New York, London; Volume I, 1962, pages 32–42 and pages 44–54 and Volume II, 1964, pages 5–6 and 198–199, and in Kunststoff-Handbuch, Volume VII, Vieweg-Hochtlen, Carl-Hanser-Verlag, Munich, 1966, e.g. on pages 45–71. The above-mentioned compounds which have a molecular weight of from 400 to 10,000 and contain at least two isocyanate-reactive hydrogen atoms may, of course, also be used as mixtures, e.g. mixtures of polyethers and polyesters.

It is particularly advantageous in some cases to use a combination of low melting and high melting polyhydroxyl compounds (German Offenlegungsschrift No. 2,706,297).

3. Compounds having a molecular weight of from 32 to 400 containing at least two isocyanate-reactive hydrogen atoms may also be used as starting components. Included are compounds containing hydroxyl groups and/or amino groups and/or thiol groups and/or carboxyl groups, preferably hydroxyl groups and/or amino groups, and they serve as chain lengthening agents or cross-linking agents. They generally have from 2–8, preferably from 2–4, isocyanate-reactive hydrogen atoms.

These may also be used as mixtures of various compounds containing at least two isocyanate-reactive hydrogen atoms and having a molecular weight of from 32 to 400.

Examples of such compounds include those mentioned on page 30 of German Offenlegungsschrift No. 2,737,951.

The low molecular weight polyols used according to the present invention may also be mixtures of hydroxyaldehydes and hydroxyketones ("formoses") or the polyhydric alcohols obtained from them by reduction ("formitol"). Examples include the compounds obtained from the autocondensation of formaldehyde hydrate in the presence of metal compounds used as catalysts and in the presence of compounds capable of enediol formation as co-catalysts (German Offenlegungsschriften Nos. 2,639,084; 2,714,084; 2,714,104; 2,721,186; 2,738,154 and 2,738,512). These formoses are advantageously used in combination with aminoplast formers and/or phosphites for obtaining synthetic products having improved flame resistance (German Offenlegungsschriften Nos. 2,738,513 and 2,738,532). Solutions of polyisocyanate polyaddition products, in particular of polyhydrazodicarbonamides and/or polyurethane ureas containing ionic groups, in low molecular weight polyhydric alcohols may also be used as polyol components according to the present invention (German Offenlegungsschrift No. 2,638,759).

Compounds which may be used as chain lengthening agents according to the present invention also include 1-mercapto-3-aminopropane, substituted or unsubstituted amino acids (such as glycine, alaminin, valine, serine and lysine) and substituted and unsubstituted dicarboxylic acids (such as succinic acid, adipic acid, phthalic acid, 4-hydroxyphthalic acid and 4-aminophthalic acid).

Compounds which are monofunctional in their reaction with isocyanates may also be used in a proportion of from 0.01 to 10% by weight, based on the polyurethane solids content, to serve as so-called chain breakers. Examples of such monofunctional compounds include monoamines such as butylamine, dibutylamine, octylamine, stearylamine, N-methylstearylamine, pyrrolidine, piperidine, cyclohexylamine, monohydric alcohols (such as butanol, 2-ethylhexanol, octanol and dodecanol), the various amyl alcohols, cyclohexanol and ethylene glycol monoethyl ether. In the process of the invention in general an index (molar ratio of total active H-atoms to NCO-groups present) of about 0,9 to about 1,1 is applied.

4. Auxiliary agents and additives which may be used include water and/or readily volatile inorganic or organic substances as blowing agents as described in German Offenlegungsschrift No. 2,737,951 (page 32) and, optionally, also known catalysts, e.g. those described in German Offenlegungsschrift No. 2,737,951 (pages 32 and 33).

The reaction between isocyanate groups and Zerewitinoff-active hydrogen atoms is also greatly accelerated by lactams and azalactams, an associate being first formed between the lactam and the compound which contains acidic hydrogen. Such associates and their catalytic action have been described in German Offenlegungsschriften Nos. 2,062,282; 2,062,289; 2,117,576 (U.S. Pat. Nos. 3,758,444); 2,129,198; 2,330,175 and 2,330,211.

All the catalysts may, of course, be used as mixtures. It is particularly interesting to use combinations of organic metal compounds with amidines, amino-pyridines or hydrazino pyridines (German Offenlegungsschriften Nos. 2,434,185; 2,601,082 and 2,603,834).

Other representatives of catalysts which may be used according to the present invention and the mode of action of the catalysts have been described in Kunststoff-Handbuch, Volume VII, published by Vieweg-Hochtlen, Carl-Hanser-Verlag, Munich, 1966, e.g. on pages 96 to 102.

The catalysts are generally used in a quantity of about 0.001 to 10% by weight, based on the total quantity of compounds having at least two isocyanate-reactive hydrogen atoms.

Surface-active additives such as emulsifiers, foam stabilizers, reaction retarders and other additives may also be used (see German Offenlegungsschrift No. 2,737,951, page 34, for information on all these additives).

Other examples of surface-active additives, foam stabilizers, cell regulators, reactive retarders, stabilizers, flame retarding substances, plasticizers, dyes, fillers and fungistatic and bacteriostatic substances which may also be used according to the present invention and details concerning their use and mode of action may be found in Kunststoff-Handbuch, Volume VII, published by Vieweg-Hochtlen, Carl-Hanser-Verlag, Munich, 1966, e.g. on pages 103–113.

EXAMPLES

EXAMPLE 1

Dimethoxyphosphonyl-N-methoxymethyl-formic acid amide 174 g (2 mols) of methoxymethyl isocyanate are added dropwise to 220 g (2 mols) of dimethylphosphite and 5 g of triethylamine, and the reaction mixture is heated to 60° C. until the band at 2150 cm$^{-1}$ due to the oscillation of the isocyanate group has disappeared from the IR spectrum. Low volatile constituents are evaporated off under vacuum.

Yield quantitative; pale yellow oil: $n_D^{20}$: 1.4515;

Analysis for $C_5H_{12}NO_5P$ (molecular weight: 197); Calculated C: 30.4, H: 6.1, N: 7.1, P: 15.7; Found: C: 31.5, H: 6.1, N: 7.8, P: 15.3.

EXAMPLE 2

Diethoxyphosphonyl-N-chlorohexyl-formic acid amide

From 138 g (1 mol) of diethylphosphite, 3 g of triethylamine and 161.5 g (1 mol) of chlorohexyl isocyanate according to Example 1.

Yield quantitative; pale yellow oil: $n_D^{20}$: 1.4678;

Analysis for $C_{11}H_{23}ClNO_4P$ (molecular weight: 299.5); Calculated: C: 44.0, H: 7.7, Cl: 11.8, P: 10.3; Found: C: 45.0, H: 8.0, Cl: 11.5, P: 10.3.

EXAMPLE 3

Diethoxyphosphonyl-N-isobutyl-formic acid amide

From 138 g (1 mol) of diethylphosphite, 3 g of triethylamine and 99 g (1 mol) of isobutyl isocyanate according to Example 1.

Yield quantitative; pale yellow oil: $n_D^{20}$: 1.4488;

Analysis for $C_{15}H_{20}NO_4P$ (molecular weight: 237); Calculated: C: 59.0, H: 6.5, N: 4.6, P: 10.1; Found: C: 58.2, H: 6.8, N: 4.9, P: 10.0.

EXAMPLE 4

N,N'-hexamethylene-bis-(diethoxyphosphonyl)-formic acid amide

From 138 g (1 mol) of diethylphosphite, 2 g of triethylamine and 84 g (0.5 mol) of hexamethylene diisocyanate according to Example 1.

Yield quantitative; pale yellow oil;

Analysis for $C_{16}H_{34}N_2O_8P_2$ (molecular weight: 444); Calculated C: 43.0, H: 8.0, N: 6.3, P: 14.1; Found: C: 43.5, H: 8.0, N: 6.5, P: 13.8.

EXAMPLE 5

Diethoxyphosphonyl-N-methoxymethyl-formic acid amide

From 138 g (1 mol) of diethylphosphite, 3 g of triethylamine and 87 g (1 mol) of methoxymethyl isocyanate as described in Example 1.

Yield quantitative; pale yellow oil;

Analysis for $C_7H_{16}NO_5P$ (molecular weight: 225); Calculated: C: 37.3, H: 7.1, N: 6.2, P: 13.8; Found: C: 38.1, H: 7.1, N: 7.2, P: 13.2.

EXAMPLE 6

Dimethoxyphosphonyl-N-chlorohexyl-formic acid amide

From 110 g (1 mol) of dimethylphosphite, 3 g of triethylamine and 161.5 g (1 mol) of chlorohexyl isocyanate as described in Example 1.

Yield 254 g, corresponding to 94% of the theoretical yield, of a pale yellow oil.

Analysis for $C_9H_{19}ClNO_4P$ (molecular weight: 271); Calculated: C: 39.8, H: 7.0, Cl: 13.1, N: 5.1, P: 11.4; Found: C: 39.2, H: 7.2, Cl: 12.8, N: 5.3, P: 11.8.

EXAMPLE 7

Diethoxyphosphonyl-N-methyl-formic acid amide

From 138 g (1 mol) of diethylphosphite, 3 g of triethylamine and 57 g (1 mol) of methyl isocyanate as described in Example 1.

Yield 150 g, corresponding to 88% of the theoretical yield of a pale yellow oil.

Analysis for $C_4H_{16}NO_4P$ (molecular weight: 167); Calculated: C: 28.8, H: 6.0, N: 8.4, P: 18.5; Found: C: 29.0, H: 6.0, N: 8.7, P: 17.4.

EXAMPLE 8

The preparation of flexible elastic polyetherpolyurethane foams capable of being high frequency welded and flame laminated by addition of the phosphonyl formic acid amide described in Examples 1 to 7 were carried out on a continuously operating high pressure machine manufactured by Henneke, Birlinghoven, Siegkreis, Federal Republic of Germany. In each case, 100 parts of a propylene oxide polyether having an OH number of 45 (started on trimethylolpropane) were used. The procedure is summarized in the table which follows. The foams obtained were welded with a line electrode having a surface area of 10 cm$^2$ under a pressure of 9 kp/cm$^2$. The samples used in each case were foam sheets each having a thickness of 10 mm (foam/foam) and a composite system consisting of a polyamide velours, an 8 mm thick foam sheet and a polyamide gauze.

The welding tension was 650 mV and the current 480 mA.

The following were also added to the formulations: 0.2 part by weight of tin(II) octoate, 0.7 part by weight of a commercial foam stabilizer, 0.6 part of dimethyl ethanolamine and 0.1 part of an amine activator (Desmorapid PS 207, Bayer AG). An isomeric mixture of 2,4- and 2,6-tolylene diisocyanate (80:20% by weight) was used (33 parts).

| Examples | 8a | 8b | 8c | 8d | 8e |
| --- | --- | --- | --- | --- | --- |
| Compound of Example 1 | — | 2.0 | 1.0 | 2.0 | 3.0 |
| Parts by weight of water | 2.5 | 2.5 | 3.0 | 3.0 | 3.0 |
| Unit weight kg/m$^3$ | 33 | 33 | 39 | 39 | 39 |
| Tensile strength (KPa) | 105 | 130 | 170 | 150 | 170 |
| Elongation at break (%) | 230 | 290 | 270 | 253 | 230 |
| Compression resistance 40 (KPa) | 3.9 | 3.5 | 3.8 | 3.7 | 3.6 |
| Pressure deformation residue 90 (%) | 3.4 | 5.8 | 4.5 | 6.1 | 4.8 |
| Decrease in compression resistance according to Ford (%) | 35 | 25 | 20 | 19 | 27 |
| Welding time foam/foam (sec.) above | 10 | 4 | 5 | 4 | 3 |
| Welding time foam/polyamide/bond (sec.) | 8 | 1.3 | 1.5 | 1.3 | 1.0 |

The foams obtained are open-celled and free from defects and can easily be flame laminated.

The welding seams obtained in Examples 8b to 8e are free from any hardened areas, clearly marked and produce firm bonding, with an interruption strength of 58 N by 5 cm seam breadth.

EXAMPLE 9

The procedure is the same as described in Example 8, using 2.5 parts of water and 33 parts of tolylene diisocyanate.

| Examples | 9a | 9b | 9c | 9d |
|---|---|---|---|---|
| Compound of Example 5 | — | 1.0 | 2.0 | 3.0 |
| Unit weight | 37 | 36 | 38 | 38 |
| Tensile strength (KPa) | 115 | 110 | 110 | 110 |
| Elongation at break (%) | 295 | 315 | 330 | 340 |
| Compression resistance (KPa) | 3.4 | 3.1 | 3.1 | 3.2 |
| Pressure deformation residue 90 (%) | 3.4 | 3.8 | 4.0 | 4.0 |
| Welding time foam/foam (sec.) over | 10 | 5 | 4 | 4 |
| Welding time foam/polyamide/bond (sec.) | 8 | 2.5 | 2.0 | 1.5 |

The welding seams obtained in Examples 9b to 9d contrast with that obtained in 9a in being clearly marked, free from hardened areas and firmly bonded, with an interruption strength of 60 N by 5 cm seam breadth.

EXAMPLE 10

The procedure is the same as described in Example 8, using 2.5 parts of water and 33 parts of tolylene diisocyanate.

| Examples | 10a | 10b | 10c | 10d |
|---|---|---|---|---|
| Compound of Example 2 | — | 1.0 | 3.0 | 5.0 |
| Unit weight (kg/m³) | 36 | 36 | 38 | 36 |
| Tensile strength | 110 | 120 | 120 | 110 |
| Elongation at break (%) | 305 | 370 | 350 | 360 |
| Compression resistance | 3.3 | 3.2 | 3.3 | 3.3 |
| Welding time foam/foam (sec.) over | 10 | 5 | 5 | 5 |
| Welding time foam/polyamide/bond (sec.) | 8 | 2.5 | 2.5 | 2.5 |

In contrast to the welding seam obtained in Example 10a, those obtained in Examples 10b to 10d are free from hardened areas, clearly marked and firmly bonded, with an interruption strength of 59 N by 5 cm seam breadth.

EXAMPLE 11

The procedure is the same as described in Example 8, using 2,5 parts of water and 33 parts of tolylene diisocyanate.

| Examples | 11a | 11b | 11c | 11d |
|---|---|---|---|---|
| Compound of Example 4 | — | 1.0 | 2.0 | 3.0 |
| Unit weight (kg/m³) | 37 | 37 | 36 | 36 |
| Tensile strength (KPa) | 115 | 120 | 120 | 115 |
| Elongation at break (%) | 310 | 315 | 320 | 310 |
| Welding time foam/foam (sec.) | 10 | 5 | 5 | 3 |
| Welding time foam/polyamide/bond (sec.) | 8 | 2 | 2.5 | 1.7 |

Foams 11b to 11d were open-celled and free from defects and the welding seam was well formed and with an interruption strength from 56 N by 5 cm seam breadth.

EXAMPLE 12

A flexible elastic polyester polyurethane foam capable of being high frequency welded was prepared using 100 parts of a polyester polyol (from adipic acid, ethylene glycol and trimethylolpropane), having an OH number of 60, 38 parts of tolylene diisocyanate, 3 parts of water, 1.5 parts of N-methylmorpholine and 3 parts of a commercial ester dispersing agent.

| Examples | 12a | 12b | 12c | 12d |
|---|---|---|---|---|
| Additive of Example 2 | — | 1.0 | 2.0 | 3.0 |
| Unit weight (kg/m³) | 34 | 35 | 35 | 35 |
| Tensile strength (KPa) | 130 | 120 | 130 | 125 |
| Elongation at break (%) | 295 | 290 | 290 | 300 |
| Welding time foam/foam (sec.) | 10 | 5 | 5 | 5 |
| Welding time foam/polyamide/bond (sec.) | 4 | 2 | 1.8 | 1.7 |

The resulting foams 12b to 12d were open-celled, free from defects and showed a well-formed seam in the welding area with an interruption strength of 60 N by 5 cm seam breadth.

What is claimed is:

1. Dialkoxy-phosphonyl-N-alkyl-formic acid amides corresponding to the formulae:

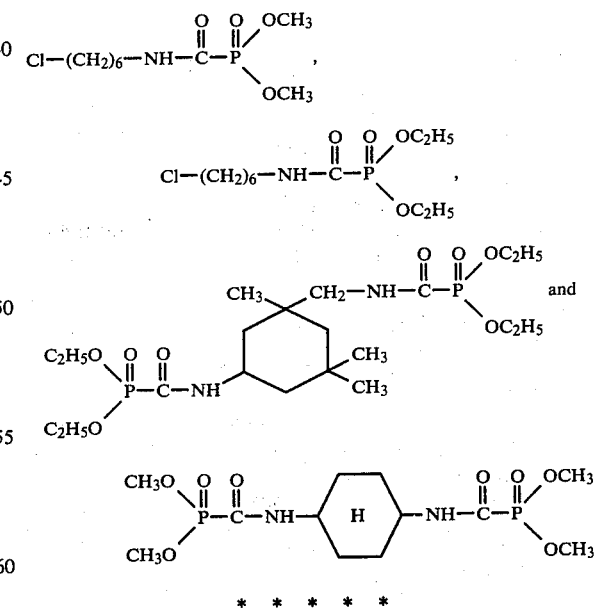

* * * * *